(12) United States Patent
Feussner et al.

(10) Patent No.: US 8,663,254 B2
(45) Date of Patent: Mar. 4, 2014

(54) BLIND RIVET FOR ADAPTING BIOLOGICAL TISSUE AND DEVICE FOR SETTING THE SAME, IN PARTICULAR THROUGH THE INSTRUMENT CHANNEL OF AN ENDOSCOPE

(75) Inventors: Hubertus Feussner, Munich (DE); Joachim Heinzl, Munich (DE); Ulrich Hausmann, Garching (DE); Robert Paspa, Kirchheim (DE)

(73) Assignee: Technische Universitaet Muenchen, Munich (DE)

( * ) Notice: Subject to any disclaimer, the term of this patent is extended or adjusted under 35 U.S.C. 154(b) by 1202 days.

(21) Appl. No.: 11/579,254

(22) PCT Filed: May 4, 2005

(86) PCT No.: PCT/DE2005/000846
§ 371 (c)(1),
(2), (4) Date: Jul. 28, 2008

(87) PCT Pub. No.: WO2005/107608
PCT Pub. Date: Nov. 17, 2005

(65) Prior Publication Data
US 2009/0054913 A1  Feb. 26, 2009

(30) Foreign Application Priority Data
May 7, 2004  (DE) .......................... 10 2004 022 590

(51) Int. Cl.
*A61B 17/08*  (2006.01)

(52) U.S. Cl.
USPC ............................ 606/151; 606/157; 606/213

(58) Field of Classification Search
USPC ......... 606/139, 142, 144, 151, 153–156, 167, 606/213, 217; 411/29, 34, 38, 43, 501; 623/23.72
See application file for complete search history.

(56) References Cited

U.S. PATENT DOCUMENTS

| | | | |
|---|---|---|---|
| 4,629,380 A * | 12/1986 | Gunkel et al. | 411/29 |
| 5,108,420 A * | 4/1992 | Marks | 606/213 |
| 5,258,011 A | 11/1993 | Drews | |
| 5,350,399 A * | 9/1994 | Erlebacher et al. | 606/213 |
| 5,368,595 A * | 11/1994 | Lewis | 606/151 |
| 5,501,695 A * | 3/1996 | Anspach et al. | 606/232 |
| 5,840,078 A * | 11/1998 | Yerys | 606/151 |
| 5,915,901 A * | 6/1999 | Aasgaard | 411/29 |
| 6,071,289 A | 6/2000 | Stefanchik et al. | |

(Continued)

FOREIGN PATENT DOCUMENTS

| EP | 0705389 B1 | 6/1994 |
|---|---|---|
| EP | 1744681 B1 | 6/2011 |
| WO | 9960931 A1 | 12/1999 |

*Primary Examiner* — Corrine M McDermott
*Assistant Examiner* — Jing Ou
(74) *Attorney, Agent, or Firm* — Karl F. Milde, Jr.; Eckert Seamans Cherin & Mellott, LLC

(57) ABSTRACT

A self-piercing blind rivet is provided for apposing biological tissue together with a device for setting the same, especially through the instrumental channel of a flexible endoscope. Without the help of further instruments, it is possible to fix, approximate and appose tissue layers, the contact force while connecting the tissue layers being adjustable. The rivets are stored in the setting device, so that they can be applied in order. The rivet and setting device enable the surgeon to combine tissue discontinuities conveniently by means of an endoscope. The surgical procedure is simplified further because the rivets can remain in the body.

9 Claims, 5 Drawing Sheets

(56) References Cited

U.S. PATENT DOCUMENTS

| | | | |
|---|---|---|---|
| 6,117,159 A * | 9/2000 | Huebsch et al. | 606/213 |
| 6,162,234 A * | 12/2000 | Freedland et al. | 606/151 |
| 6,241,732 B1 | 6/2001 | Overaker et al. | |
| 6,270,500 B1 * | 8/2001 | Lerch | 606/324 |
| 6,319,258 B1 * | 11/2001 | McAllen et al. | 606/104 |
| 6,406,234 B2 * | 6/2002 | Frigg | 411/42 |
| 6,626,917 B1 * | 9/2003 | Craig | 606/144 |
| 6,796,759 B2 * | 9/2004 | Aasgaard | 411/29 |
| 6,962,591 B2 * | 11/2005 | Lerch | 606/324 |
| 7,766,939 B2 * | 8/2010 | Yeung et al. | 606/232 |
| 8,137,042 B2 * | 3/2012 | Severns | 411/387.1 |
| 2001/0037130 A1 | 11/2001 | Adams | |
| 2003/0125755 A1 | 7/2003 | Schaller et al. | |
| 2003/0164304 A1 * | 9/2003 | Imran et al. | 205/317 |
| 2004/0034375 A1 * | 2/2004 | Ruiz et al. | 606/151 |
| 2004/0044364 A1 | 3/2004 | DeVries et al. | |
| 2004/0204723 A1 * | 10/2004 | Kayan | 606/151 |
| 2004/0223832 A1 * | 11/2004 | Aasgaard | 411/501 |
| 2004/0225292 A1 * | 11/2004 | Sasso et al. | 606/73 |
| 2005/0131460 A1 * | 6/2005 | Gifford et al. | 606/215 |
| 2005/0171562 A1 * | 8/2005 | Criscuolo et al. | 606/151 |
| 2005/0228413 A1 * | 10/2005 | Binmoeller et al. | 606/153 |
| 2009/0024149 A1 | 1/2009 | Saeed et al. | 606/151 |

* cited by examiner

BLIND RIVET FOR ADAPTING BIOLOGICAL TISSUE AND DEVICE FOR SETTING THE SAME, IN PARTICULAR THROUGH THE INSTRUMENT CHANNEL OF AN ENDOSCOPE

BACKGROUND OF THE INVENTION

The invention relates to a self-piercing blind rivet for apposing biological tissue and to a device for setting the same, especially through the instrument channel of a flexible endoscope, in order to connect layers of tissue with an adjustable contacting force.

Blind rivets are usually used to connect metal sheets, predominantly in aircraft construction. However, they can also be used for other materials, such as plastics, wood or leather. Their great advantage over other forms of rivets is that the parts to be joined have to be accessible only from one side, since there is no need for a bottom die to close the rivet. For most blind rivets, holes, which are one above the other for setting the rivet, must be drilled to start with. There are, however, also blind rivets, for example, in the EP 0 705 389 B1, which are self piercing in that they pierce the parts to be joined automatically during the setting process.

In surgery also, there are first indications of the use of blind rivets. Their applications are limited, however, mainly to fixing implants or tissue to bones, as described in U.S. Pat. No. 6,241,732 B1 or the WO 99/62418. A corneal rivet (U.S. Pat. No. 5,258,011), by means of which it is possible to close cuts in the cornea of the eye, is also worth mentioning. This rivet, however, mainly is not constructed as a blind rivet and must instead be serviced from both sides, which makes use in endoscopy difficult and requires an additional instrument.

Suturing techniques are mainly used in medicine for apposing tissue. For example, attempts have been made to develop suturing devices for minimally invasive surgery to close off tissue discontinuities when operating on the gastrointestinal tract. Since the needle can no longer be guided with the fingers here, this guidance must be taken over by grippers. However, since these grippers do not attain even approximately the freedom of movement and the movement possibilities of the hand, this suturing is very difficult, uncertain and time consuming. For this reason, different devices for automated suturing have been planned and, in some cases, put into practice. U.S. Pat. No. 6,071,289 is an example of this. However, even with such a device, the most serious disadvantage of the suturing technique, namely, the knotting of the suture, cannot be eliminated. For this purpose, either a knot is made outside of the body and pushed through the instrument channel or the suture is knotted laboriously with grippers. Accordingly, because of their complexity and the therefrom resulting overall size, it has not yet been possible to insert such devices into the instrument channels of flexible endoscopes.

Because of the disadvantages of suturing devices, clamps and clips were developed as alternatives. These consist essentially of two arms, which are connected to one another and with which the tissue can be held together, as disclosed in the German patents 299 23 545 U1 or 102 03 956 A1. Since the arms can be expanded only to a very limited extent for this purpose, it is necessary that the tissue parts, which are to be joined, be approximated with a further device before the application, so that use by means of an endoscope is prevented.

The connecting element of the US patent application 2003/0125755 is a combination of a clip and a suturing method. A clip, which is detached from a suture with pliers, hangs at the end of a needle with suture. In this way, the problem of the knot is overcome. Once again, however, it is necessary to use a further instrument, so that the instrument channel of an endoscope cannot be used by itself.

The WO 99/60931 application represents a further embodiment, which may be regarded as a blind rivet. The clip here consists of a carrier, a distal fixing element and a proximal fixing element. For the function, a connecting sleeve between the two fixing elements is also provided here. The sleeve determines the distance between the fixing elements. For this reason, the extent of the tissue approximation is fixed. It is therefore not possible to connect tissues of different or unknown thicknesses using one and the same clip. This represents a major limitation for the surgeon. Associated with this is the fact that the contacting force, with which the tissue is held together, is also not adjustable, so that the surgeon cannot gain any feeling for the quality of the connection. Moreover, the functional reliability of the clip is also a cause for concern, since a stop has not been provided for the proximal fixation element, so that it may happen that the complete clip can be pushed through the tissue and, as it were, fall out on the other side. It is also not possible here to load the clips into a magazine, that is, to set several clips consecutively with one instrument. For reloading, the whole instrument must be exchanged or, at the very least, removed from the endoscope.

SUMMARY OF THE INVENTION

It is a principal object of the invention to avoid the aforementioned disadvantages by means of a connecting element and a device for setting such elements. A further object is to provide a blind rivet which can connect any number of tissue layers of any thickness with a contacting force, which can be set by the surgeon, and to provide a setting device that is suitable for use in the instrument channel of a conventional, flexible endoscope.

The blind rivet according to the invention has a carrier, at the distal end of which is disposed a fixed clip, the tip of the carrier being constructed as a needle, with which the tissue is pierced. After the tissue is pierced, the distal, fixed clip comes into contact with the tissue and prevents the possibility of retracting the rivet. A holding device, which is supported at the opposite side of the tissue and, with that, fixes the position of the rivet, is provided on the proximal side of the carrier. This proximal holding device usually is a clip, the structure of which is similar to that of the fixed, distal clip, if only the approximation of the tissue layers matters.

The holding device may, however, also be a different device, or combined with this; accordingly, it is also possible to construct this holding device as a medication dispenser, as a diagnosis device with telemetric transfer, etc.

The invention is described in greater detail in the following with reference to the attached drawings, which show several, non-limiting embodiments. In the drawings, For a full understanding of the present invention, reference should now be made to the following detailed description of the preferred embodiments of the invention as illustrated in the accompanying drawings.

DESCRIPTION OF THE PREFERRED EMBODIMENTS

Figure 1:
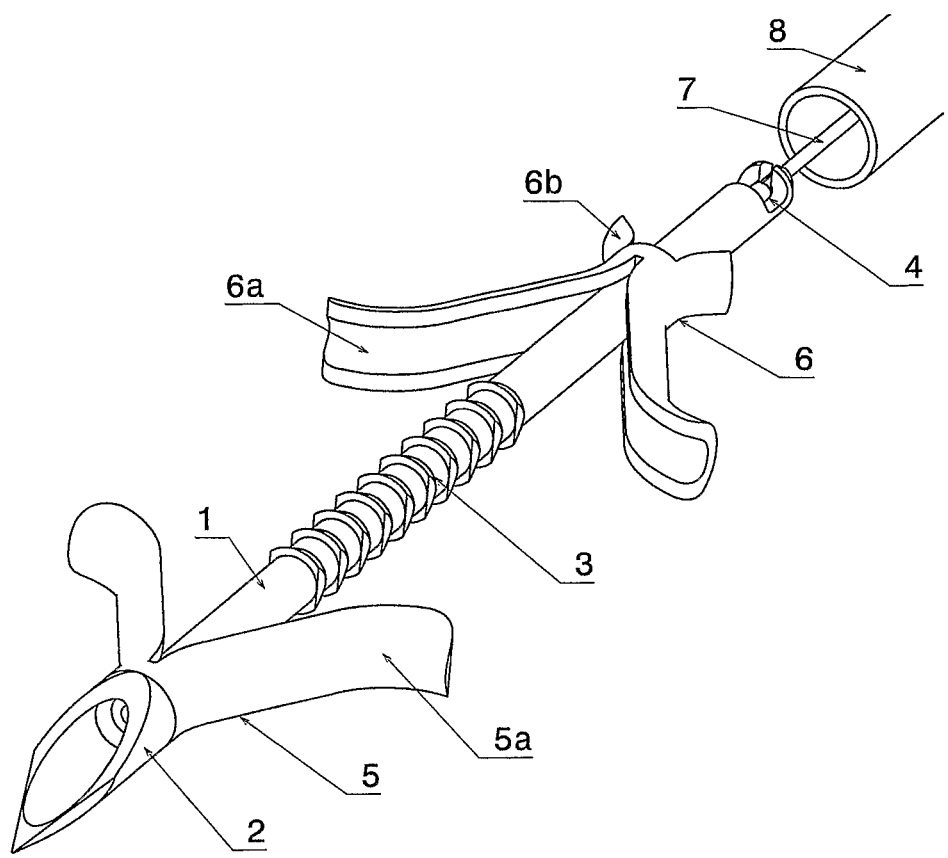
FIG. 1 shows the construction of a self-piercing blind rivet according to a preferred embodiment of the present invention.

The preferred embodiments of the present invention will now be described with reference to FIGS. 1-11 of the drawings. Identical elements in the various figures are designated with the same reference numerals.

The rivet, as shown in its relaxed form in FIG. 1, consists essentially of three parts. A tubular carrier 1 is provided at the distal end with a tip 2, in the middle part with an arresting castellation 3 and, at the proximal end, with a coupling element 4. Two clips 5 and 6 are mounted on the carrier, the distal clip 5 being axially fixed and the proximal clip 6 being displaceable in the distal, axial direction and being held in the opposite direction by the arresting castellation. The distal clip consists of a basic, cylindrical body from which two arms 5a branch out. The proximal clip also consists of a basic, cylindrical body, from which two arms 6a, as well as two wings 6b spread out. Within the carrier, there is an actuating element 7 with a latch at the distal end, with which it can hook into the coupling element and pull the carrier in the proximal direction. This actuating element is guided by a guiding tube 8.

Figure 2:
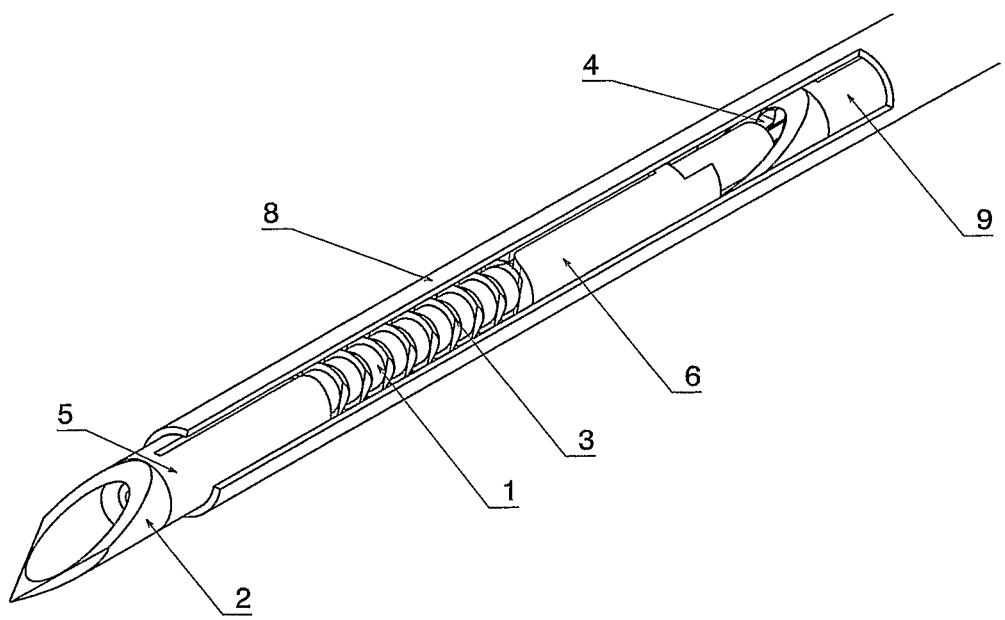
FIG. 2 shows the rivet of FIG. 1 in the retracted state.

In the closed state, as shown in FIG. 2 with the guiding tube 8 cut open, the two clips 5 and 6 contact the carrier 1 due to elastic deformation, so that the rivets in the guiding tube can be shifted. The rivets are inserted one into the other in such a manner, that the proximal end of the leading rivet is seated in the tip of the rivet 9 that follows. Accordingly, the rivets can be advanced by pushing the carrier of the last rivet in the series. It is also possible to retract the rivets, since the actuating element 7 is hooked into the coupling element 4 of the first rivet. Due to the fact that the rivets are plugged one into the other and because there is clearance, a joint results, which, together with the elasticity of the carrier, maintains the mobility of the instrument channel of the endoscope. Due to the geometry of the tip and a covering for the tip, it is avoided that the latter damages the guiding tube, especially when this tube is curved.

Figure 3:
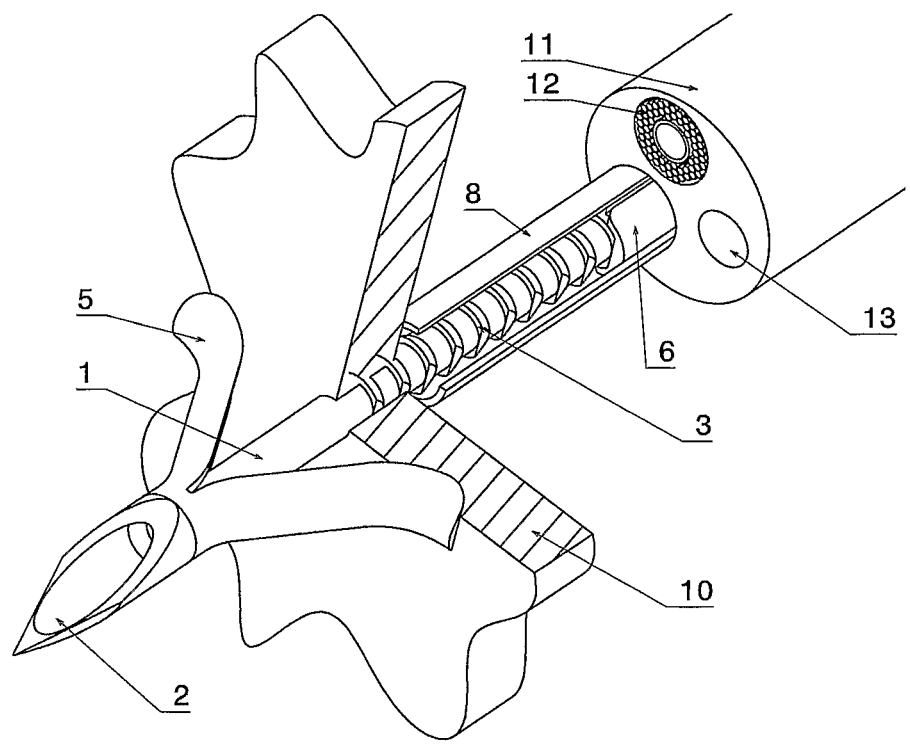
FIG. 3 shows a first tissue flap threaded and fixed.

If the rivet is pushed out of the guiding tube 8, the distal clip 5 opens up, as can be seen in FIG. 3, due to the elastic pre-tension or due to the memory effect of the shape-memory materials. Tissue layers 10 are pierced in sequence with the tip 2 and secured by the distal clip and the guiding tube. By these means, it is possible to approximate the tissue layers with the rivet device without additional instruments.

It is also possible to use a dolly, which is guided, for example, in the instrument channel of the endoscope and embraces the tissue layers that are to be approximated, for setting the rivet, so that, when pierced with the needle, the tissue cannot move out of the way. The needle with the blind rivet can be guided in the same instrument channel within the dolly; a further instrument channel may also be provided for this purpose.

Moreover, an endoscope 11, in the instrument channel of which there is the riveting device, is shown in FIG. 3. It is equipped with an optical system 12 and a flushing channel 13. Accordingly, the riveting device is in the visual range of the endoscope. The instrument channel of the endoscope can also assume the task of the guiding tube.

Figure 4:
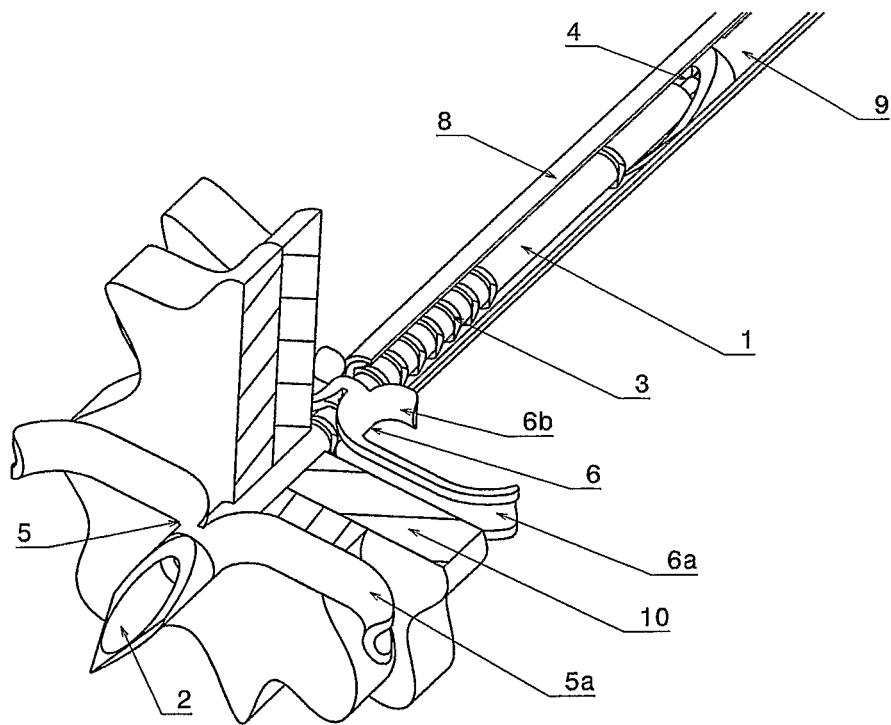
FIG. 4 shows the closing of the rivet.

As can be seen in FIG. 4, the rivet is closed owing to the fact that the rivet is pushed out of the guiding tube 8 until the arms 6a and then the wings 6b open up. The proximal clip 6 is supported with the wings at the guiding tube, when the carrier 1 is pulled in the proximal direction. This takes place by pulling at the actuating element 7, which is hooked into the coupling element 4. In this way, the proximal clip is pushed over the arresting castellation 3. At the same time, the arms 5a and 6a contact the tissue 10 and spread out as the contacting pressure is continued, until they are at an angle of about 90° to the carrier. During this process, the contacting pressure on the tissue layers is increased continuously. As the tightening is continued, the elasticity of the tissue is utilized in order to increase the contacting force further.

Figure 5:
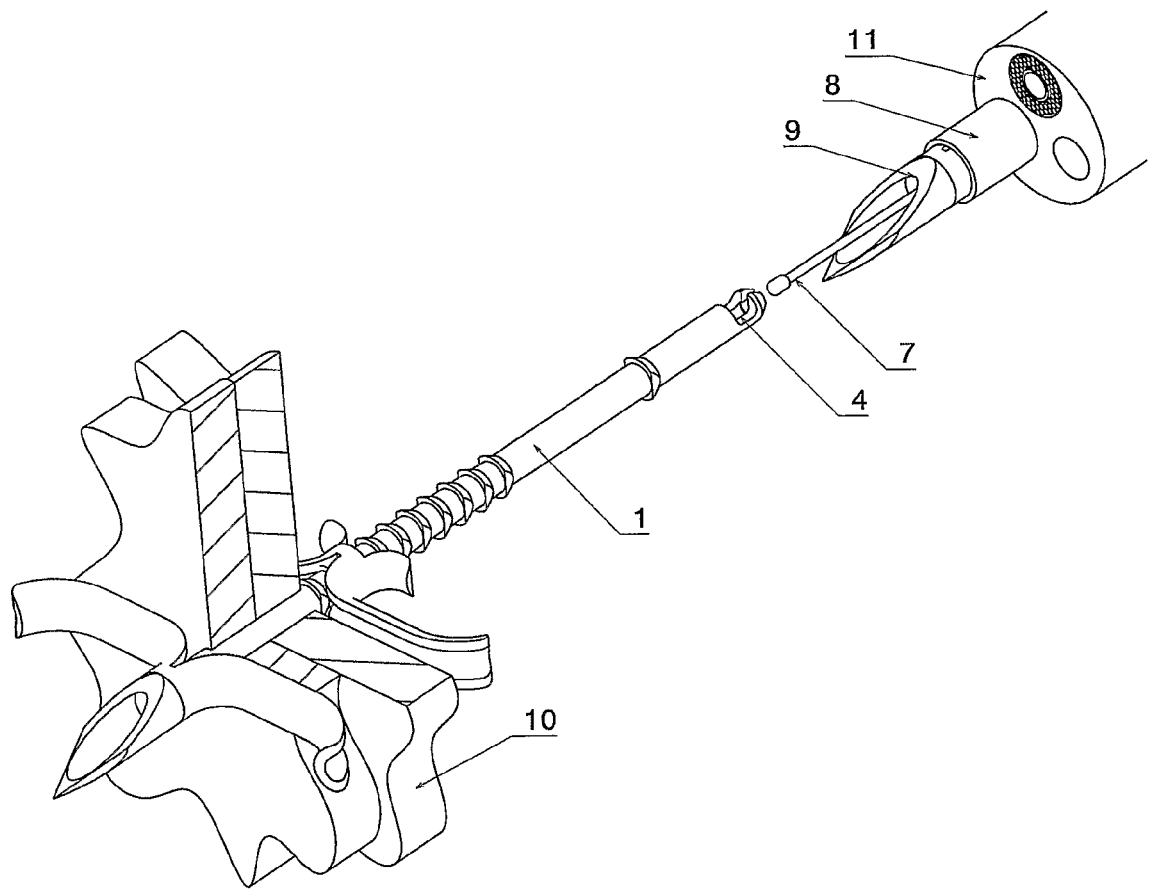
FIG. 5 shows the rivet in the applied state.

As can be seen in FIG. 5, in order to detach the rivet from the device, the actuating element 7 is left loose and the guiding tube 8 is pulled slightly in the proximal direction. As a result, the rivet 9 that follows is detached from the one recently applied. With that, the coupling element 4 is released and the actuating element can be uncoupled. The rivet has now been applied completely. The actuating element is then pulled in the proximal direction, until it is coupled to coupling element of the next rivet. The rivets are pushed in the guiding tube in the distal direction, until the distal clip of the next rivet opens up, so that this rivet is ready to be applied.

Figure 6:
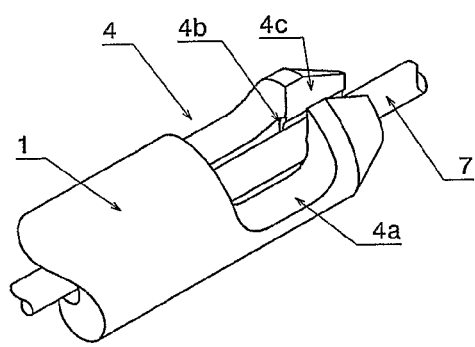
FIG. 6 shows the recess with the actuating element.
Figure 7:
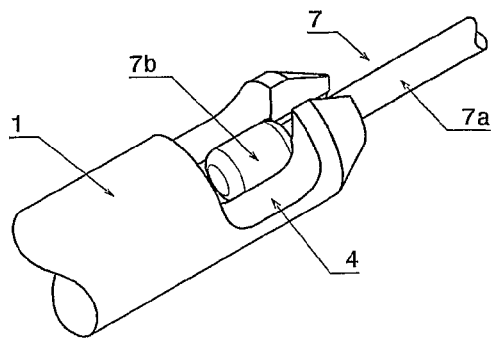
FIG. 7 shows the snapping into place of the actuating element in the recess.
Figure 8:
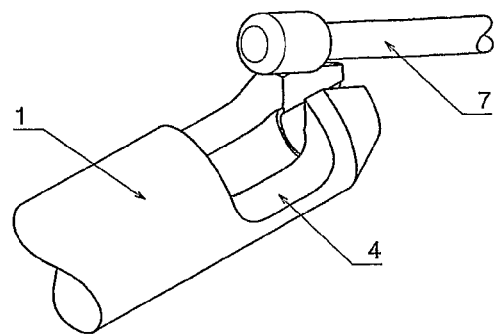
FIG. 8 shows the uncoupling of the actuating element from the recess.

The construction of the coupling element 4 at the proximal end of the carrier 1 is shown in FIG. 6. It consists of a recess 4a, a stop 4b and a groove 4c. The actuating element 7 passes through the coupling element. As can be seen in FIG. 7, there is a lock 7b at the distal end of the actuating element 7, which essentially is a pull rope 7a. This lock hooks into the stop of the coupling, when the actuating element is pulled. If the actuating element is left loose, as can be seen in FIG. 8, and tilted with respect to the carrier, the lock detaches from the stop, so that the rivet is detached from the actuating element and, accordingly, from the device as a whole.

The tip 2 of an applied rivet represents a danger for the surrounding tissue and can lead to mechanical irritation (bleeding, perforation) of the same. There are several possibilities for avoiding this. According to the first possibility, the tip is produced from a bioabsorbable material, which is broken down within a few days or hours by the body; this is the case, for example, with various magnesium alloys, such as AZ91. Plastics, such as different lactides, are also suitable for this purpose. However, magnesium alloys offer the advantage of a hardness, which is required for puncturing the tissue and passing through it.

Figure 9:
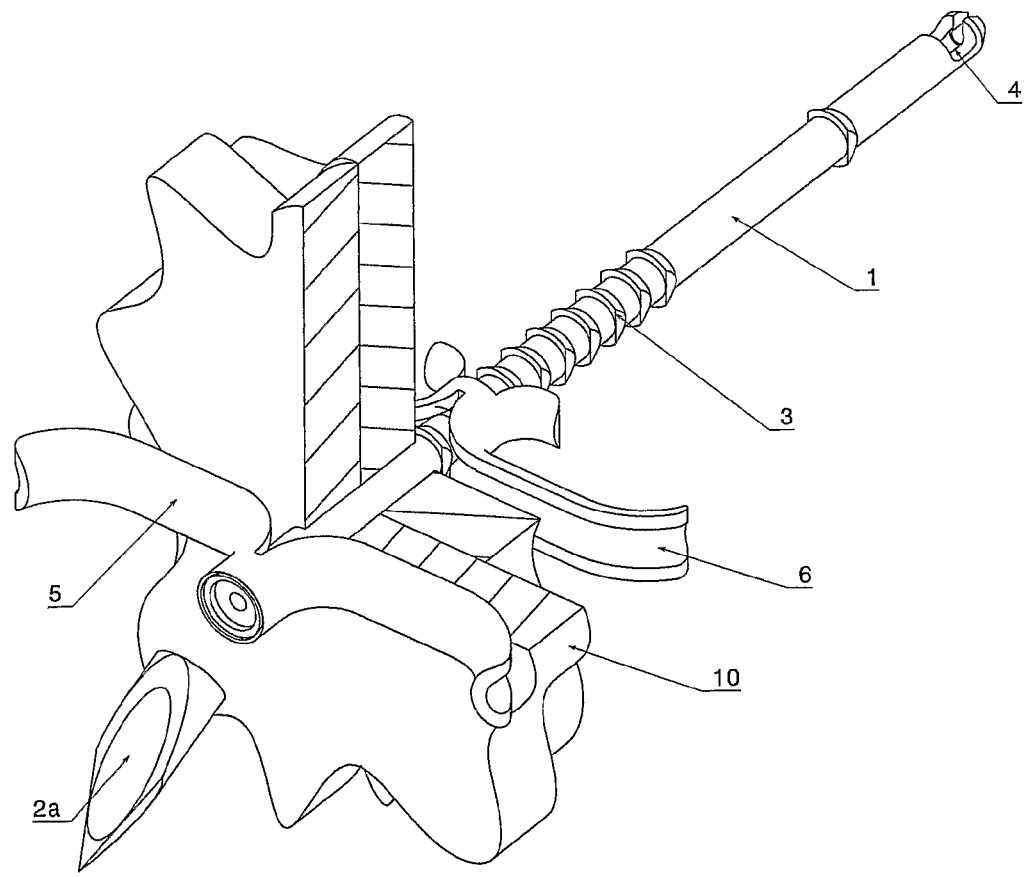
FIG. 9 shows the ejection of the tip.
Figure 10:
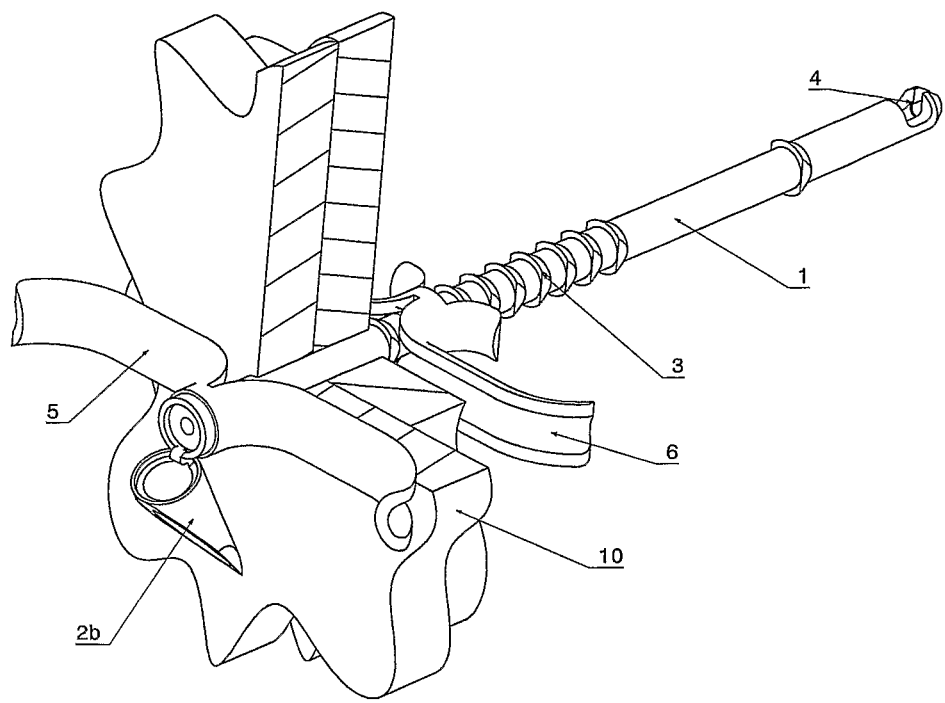
FIG. 10 shows the folding over of the tip.
Figure 11:
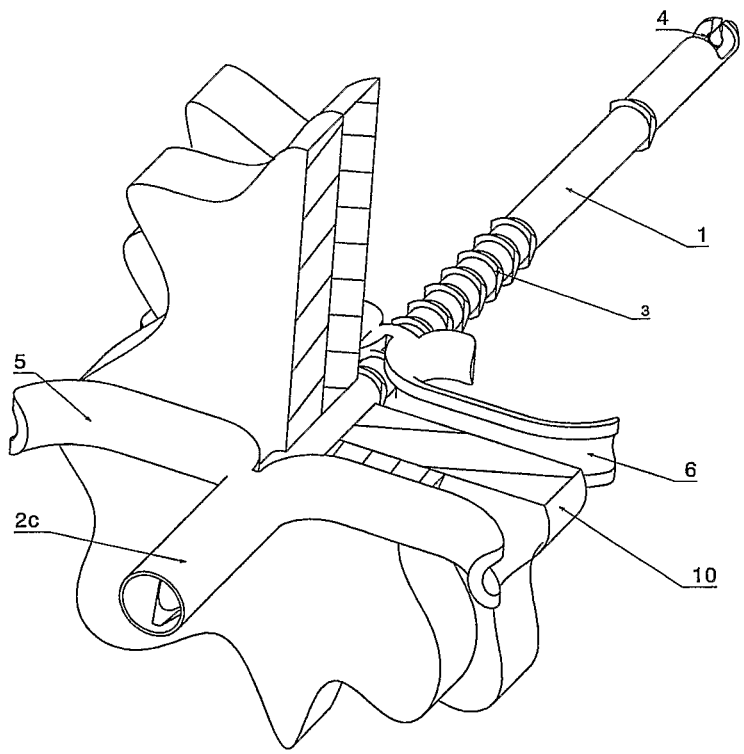

According to FIG. 9, the tip can also be cast off. This can be realized in that the tip is pushed onto the carrier 1 and, during the closing of the rivet, the distal clip 5 pushes the tip down from the carrier. If the rivet is used in the gastrointestinal tract, the cast off tip is excreted. A further possibility, as in FIG. 10, consists therein that the tip is folded back and, with that, the danger of traumatizing is decreased. Hiding the tip, as shown in FIG. 11, represents the last possibility. The basic cylindrical body of the distal clip 5 is elongated with a sleeve, which is pushed over the tip while the rivet is being closed, hiding the tip and keeping it away from the adjacent tissue.

The materials used are of great importance. Biocompatible materials must be used for all components of the rivet, that is, for the carrier 1, the tip 2 and the two clips 5, 6, in order to avoid information. Moreover, it is desirable that the rivet can remain in the body and is broken down at the conclusion of the wound healing process. For this reason, the carrier 1 is produced from bio-absorbable poly-(D/L)-lactide, which is broken down after several months. The two clips are produced from an aliphatic polyether-based or polycarbonate-based TPU. As already mentioned, the AZ91 magnesium alloy should be used if the tip is to be absorbed very rapidly. The actuating element 7 is produced from spring steel, in order to be able to transfer tensile forces. A low-friction plastic, such as PTFE, is suitable for the guiding tube 8.

As already mentioned above, instead of the second clip, a different type of holder or a device may be provided, such as a medication dispenser, etc. In this case, the distal clip is used essentially for fixing the device in the tissue.

There has thus been shown and described a novel blind rivet for apposing biological tissue and device for setting the same which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A self-piercing blind rivet for clamping opposing layers of tissue comprising, in combination:
  (a) an elongate carrier having a distal end and proximal end, the carrier being configured as a hollow tubular body with a sharp, hollow, open-ended tip at the distal end thereof and adapted to penetrate the opposing layers and to allow passage therethrough of an actuating element;
  (b) an elastically deformable distal clip fixed axially on the carrier adjacent its distal end;
  (c) an elastically deformable proximal clip disposed on the carrier and axially displaceable in a direction toward the distal end of the carrier;
  (d) a coupling element on the proximal end of the carrier adapted to receive a locking element at a distal end of the actuating element for displacing the clips relative to each other;
  wherein the actuating element with its locking element is configured to pass through the entire length of the hollow tubular body of the carrier and extend out of the tip;
  wherein the blind rivet is configured to be held in a guide tube from which it can be pushed out for penetrating the tissue;
  wherein the elastically deformable clips are configured to be pressed down around the carrier while in the guide tube and to open outward after the blind rivet has been pushed out; and
  wherein the tip attaches to and extends distally from the elastically deformable distal clip.

2. The blind rivet of claim 1, wherein at least the carrier is made of a biocompatible and bioabsorbable material.

3. The blind rivet of claim 2, wherein the tip of the carrier is made of an absorbable magnesium alloy.

4. The blind rivet of claim 3, wherein the magnesium alloy is magnesium A291.

5. The blind rivet of claim 1, wherein the distal end is bioabsorbable significantly more rapidly than the rest of the rivet in order to minimize traumatization of the tissue and any organs surrounding the tissue.

6. The blind rivet of claim 1, wherein the distal end is sheddable in order to minimize traumatization of the tissue and any organs surrounding the tissue.

7. The blind rivet according to claim 1, wherein locking teeth are located on the carrier which allows axial relative movement of the proximal clip only in the direction toward the distal end.

8. The blind rivet according to claim 1, the coupling element is configured to close the blind rivet when pulled with the actuating element, whereby the proximal clip is displaced in the direction, toward the distal end.

9. The blind rivet of claim 1, wherein the blind rivet is configured to be stacked with a plurality of such blind rivets on and along the actuating element, one into the other, in such a manner that the proximal end of a leading blind rivet is seated in the tip of a rivet that follows with a clearance, with the actuating element passing through all stacked blind rivets;
  wherein the actuating element is configured to be retracted and its locking element coupled with the coupling element of the next blind rivet that follows.

* * * * *